United States Patent [19]

Fuso et al.

[11] Patent Number: 5,578,667

[45] Date of Patent: Nov. 26, 1996

[54] SULPHONATED PHENOLIC TRIAZINE ANTIOXIDANTS FOR POLYAMIDE FIBERS

[75] Inventors: Francesco Fuso, Therwil; Gerhard Reinert, Allschwil, both of Switzerland

[73] Assignee: Ciba-Geigy Corporation, Tarrytown, N.Y.

[21] Appl. No.: 528,587

[22] Filed: Sep. 15, 1995

[30] Foreign Application Priority Data

Sep. 19, 1994 [CH] Switzerland ............... 2851/94

[51] Int. Cl.$^6$ ............ C08K 5/3492; C07D 403/00; D06P 5/02
[52] U.S. Cl. ............ 524/100; 8/442; 8/490; 8/566; 524/96; 544/113; 544/197; 544/198; 544/199; 544/210; 544/211; 544/212; 544/213
[58] Field of Search ............ 524/100, 96; 544/198, 544/113, 197, 199, 209, 210, 211, 212, 208, 212, 213; 8/490, 442, 566

[56] References Cited

U.S. PATENT DOCUMENTS

| | | | |
|---|---|---|---|
| 5,086,173 | 2/1992 | Tritschler et al. | 544/211 |
| 5,160,346 | 11/1992 | Fuso et al. | 8/442 |
| 5,181,935 | 1/1993 | Reinert et al. | 8/442 |
| 5,221,287 | 6/1993 | Reinert | 8/442 |
| 5,229,512 | 7/1993 | Slongo et al. | 544/215 |
| 5,312,917 | 5/1994 | Fuso et al. | 544/198 |
| 5,376,710 | 12/1994 | Slongo et al. | |

FOREIGN PATENT DOCUMENTS

| | | |
|---|---|---|
| 0453405 | 10/1991 | European Pat. Off. . |
| 0457730 | 11/1991 | European Pat. Off. . |

*Primary Examiner*—Veronica P. Hoke
*Attorney, Agent, or Firm*—Kevin T. Mansfield

[57] ABSTRACT

The invention relates to novel water-soluble antioxidants of formula

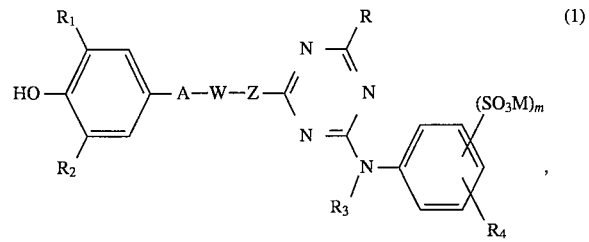

(1)

wherein the variables are as defined in the claims, to a process for their preparation and to the use thereof for the photochemical and thermal stabilisation of dyed and undyed polyamide fibre materials.

18 Claims, No Drawings

SULPHONATED PHENOLIC TRIAZINE ANTIOXIDANTS FOR POLYAMIDE FIBERS

The present invention relates to novel water-soluble antioxidants, to a process for their preparation and to the use thereof for the photochemical and thermal stabilisation of polyamide fibre materials.

In EP-A-0 466 647 or EP-A-0 459 950 it is taught to stabilise polyamide fibres photochemically and thermally by treating them with specific compounds of the class of the sterically hindered amines (HALS stabilisers). It has been found, however, that the degree of stabilisation achieved by this means does not in all cases fully meet the most exacting demands made of it. There is therefore a need to provide compounds that afford enhanced protection of polyamide fibre materials against the action of light and heat.

It is the object of this invention to provide novel compounds that meet these demands.

The novel water-soluble antioxidants are distinguished by particularly good fibre affinity and good exhaustion, especially in the neutral pH range.

Accordingly, the invention relates to novel water-soluble antioxidants of general formula $$\text{(1)}$$

wherein
R is halogen; $C_1$–$C_5$alkyl; phenyl-$C_1$–$C_5$alkyl; $C_1$–$C_5$alkoxy in which, from $C_2$, the alkyl chain may be interrupted by an oxygen or a sulfur atom; $C_3$–$C_5$alkenyloxy; $C_4$–$C_8$cycloalkoxy; amino; mono- or di(phenyl-$C_1$–$C_5$alkyl)amino; unsubstituted or hydroxy- or carboxy-substituted mono- or di-$C_1$–$C_5$alkylamino, in which the alkyl chain may be interrupted by an oxygen or a sulfur atom or by $SO_2$; mono- or di-$C_3$–$C_5$alkenyl-amino; unsubstituted or $C_1$–$C_5$alkyl-substituted mono- or di-$C_4$–$C_8$cycloalkylamino; unsubstituted phenoxy or phenoxy which is substituted by halogen, $C_1$–$C_5$alkyl, $C_1$–$C_5$alkoxycarbonyl, $C_1$–$C_5$alkoxy, carboxy, carbamoyl, mono- or di-$C_1$–$C_5$alkanoyl-amino or $C_1$–$C_5$alkanoyl; phenyl; phenylthio; phenyl-$C_1$–$C_5$alkylthio; $C_1$–$C_5$alkylthio; $C_4$–$C_8$cycloalkylthio; unsubstituted or $C_1$–$C_5$alkyl-, hydroxy- or carboxy-substituted 1-azacycloalkyl; unsubstituted or $C_1$–$C_5$alkyl-substituted morpholino; a radical of formula $$\text{(2)}$$

a radical of formula $$\text{(3)}$$

or a radical of formula $$\text{(4)}$$

wherein
one of the two substituents $R_1$ and $R_2$ is hydrogen; $C_1$–$C_8$alkyl; $C_5$–$C_7$cycloalkyl; phenyl-$C_1$–$C_4$alkyl or phenyl; and the other substituent $R_1$ or $R_2$ is $C_1$–$C_8$alkyl; $C_5$–$C_7$cycloalkyl; phenyl-$C_1$–$C_4$alkyl or phenyl;

$R_3$ is hydrogen or $C_1$–$C_4$alkyl;

$R_4$ is hydrogen; halogen; hydroxy; $C_1$–$C_5$alkyl; $C_1$–$C_5$alkoxycarbonyl; $C_1$–$C_5$alkoxy; $C_1$–$C_5$alkanoyl; carboxy; amino; mono- or di-$C_1$–$C_5$alkylamino; or mono- or di-$C_1$–$C_5$-alkanoylamino;

$R_5$ is hydrogen; oxyl; hydroxy; $C_1$–$C_5$alkyl; $C_2$–$C_5$alkenyl; $C_1$–$C_5$alkoxy; $C_1$–$C_5$alkanoyl; benzoyl or benzyl;

m is 0, 1 or 2;
n is 0, 1 or 2;
and the sum m+n is 1, 2, 3 or 4;

M may be the same or different and is hydrogen: an alkali metal, alkaline earth metal or ammonium cation or an organic ammonium cation of formula $$(C_1\text{–}C_4\text{alkyl})_a(H)_b N^+,$$

wherein
a is an integer from 0 to 3;
b is an integer from 1 to 4; and the sum of a+b=4;

A is a direct bond or unsubstituted or phenyl-substituted $C_1$–$C_8$alkylene in which, from $C_2$, the alkylene chain may be interrupted by an oxygen or a sulfur atom, and, from $C_3$, the alkylene chain may be straight or branched;

B is oxygen or —N($R_6$)—, wherein $R_6$ is hydrogen or $C_1$–$C_6$alkyl;

W is a direct bond; —O—CO—; —NH—CO—; —CO—NH—G—; or —CO—O—G—, wherein G is a direct bond, $C_1$–$C_6$alkylene, $C_5$–$C_8$cycloalkylene, phenylene or the radical —$CH_2$—$C_6H_4$—$CH_2$—, and —CO—NH—G— is able to form a ring with Z;

and
Z is oxygen, sulfur or —N($R_7$)—, wherein $R_7$ is hydrogen, $C_1$–$C_4$alkyl, allyl or benzyl.

R defined as $C_1$–$C_5$alkylthio is typically methylthio, ethylthio, propylthio or butylthio.

R defined as $C_4$–$C_8$cycloalkoxy is typically cyclobutoxy, cyclopentyloxy, methylcyclohexyloxy, ethylcyclohexyloxy, cycloheptyloxy, cyclooctyloxy or, preferably, cyclohexyloxy.

R defined as mono- or di-$C_4$–$C_8$cycloalkylamino is typically monocyclohexylamino or, preferably, dicyclohexylamino.

R defined as $C_4$–$C_8$cycloalkylthio is typically cycloheptylthio or, preferably, cyclohexylthio.

R defined as mono- or di-$C_3$–$C_5$alkenylamino is typically monobutenylamino, monoallylamino, diallylamino or dibutenylamino. Among these radicals, monoallylamino or diallylamino is preferred.

R in the significance of phenyl-$C_1$–$C_5$alkyl may typically be phenethyl, phenylpropyl, phenylbutyl or, preferably, benzyl.

R defined as mono- or di(phenyl-$C_1$–$C_5$alkyl)amino is typically monobenzylamino, monophenethylamino, dibenzylamino, diphenethylamino or benzylphenethylamino.

R defined as phenyl-$C_1$-$C_5$alkylthio is typically benzylthio or phenethylthio.

R defined as 1-azocycloalkyl is typically 1-pyrrolidyl or piperidino.

R defined as phenoxy may be substituted by one or more than one of the cited substituents.

R defined as $C_3$-$C_5$alkenyloxy will typically be butenyloxy or allyloxy.

R and $R_4$ defined as mono- and di-$C_1$-$C_5$alkylamino will typically be N-methylamino, N,N-dimethylamino, N-ethylamino, N,N-diethylamino, N,N-dipropylamino or N-methyl-N-ethylamino.

R and $R_4$ defined as halogen will conveniently be taken to mean fluoro, bromo and, preferably, chloro.

R, $R_4$ and $R_5$ defined as $C_1$-$C_5$alkoxy will typically be methoxy, ethoxy, isopropoxy, isobutoxy, tert-butoxy or tert-amyloxy.

R, $R_4$ and $R_5$ defined as $C_1$-$C_5$alkyl will typically be methyl, ethyl, n-propyl, isopropyl, n-butyl, isobutyl, sec-butyl, tert-butyl, amyl or isoamyl.

$R_1$ and $R_2$ defined as $C_1$-$C_8$alkyl will typically be methyl, ethyl, n-propyl, isopropyl, n-butyl, isobutyl, sec-butyl, tert-butyl, pentyl, hexyl, heptyl or octyl. Preferred meanings are methyl, ethyl, n-propyl, isopropyl, n-butyl, isobutyl, sec-butyl and tert-butyl. Methyl and tert-butyl are most preferred.

$R_1$ and $R_2$ defined as phenyl-$C_1$-$C_4$alkyl will typically be phenethyl, phenylpropyl, phenylbutyl or, preferably, benzyl.

$R_1$ and $R_2$ defined as $C_5$-$C_7$cycloalkyl are typically cyclopentyl, cyclohexyl, methylcyclohexyl or cycloheptyl.

$R_3$ and $R_7$ defined as $C_1$-$C_4$alkyl are typically methyl, ethyl, n-propyl, isopropyl, n-butyl, isobutyl, sec-butyl or tert-butyl.

$R_4$ in the significance of mono- or di-$C_1$-$C_5$alkanoylamino will typically be formylamino, acetylamino, propionylamino, butyrylamino, diformylamino, diacetylamino, dipropionylamino, dibutyrylamino or formylacetylamino.

$R_4$ defned as $C_1$-$C_5$alkoxycarbonyl is typically methoxycarbonyl, ethoxycarbonyl, propoxycarbonyl, butoxycarbonyl or pentoxycarbonyl.

$R_4$ and $R_5$ defined as $C_1$-$C_5$alkanoyl is typically formyl, acetyl, propionyl or n-butyryl.

$R_5$ defined as $C_2$-$C_5$alkenyl is typically vinyl, butenyl or, preferably, allyl.

$R_5$ defined as $C_1$-$C_5$alkanoyl is typically formyl, acetyl, propionyl or n-butyryl.

$R_5$ in the significance of oxyl will be understood as meaning an oxygen radical attached to the nitrogen atom.

$R_6$ defined as $C_1$-$C_6$alkyl is typically methyl, ethyl, n-propyl, isopropyl, n-butyl, isobutyl, sec-butyl, tert-butyl, pentyl or hexyl.

A defined as $C_1$-$C_8$alkylene is typically methylene, ethylene, propylene, tetramethylene, pentamethylene or hexamethylene.

G defined as $C_1$-$C_6$alkylene is typically methylene, ethylene, propylene, tetramethylene, pentamethylene or hexamethylene.

G defined as $C_5$-$C_8$cycloalkylene is typically cyclopentylene, cyclohexylene, cycloheptylene or cyclooctylene.

Illustrative examples of alkali metal ions M are the lithium, sodium or potassium cation. The sodium cation is preferred. Illustrative examples of alkaline earth metal ions are the calcium and the magnesium cation.

M as ammonium cation of formula $(C_1-C_4alkyl)_a(H)_bN^+$ is suitably trimethylammonium or, preferably, triethylammonium.

Preferred embodiments of the novel compounds relate to compounds of formula (1), wherein a) R is a radical of formula

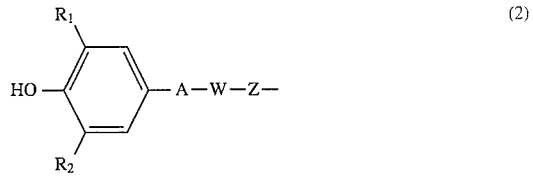

(2)

wherein one of the two substituents $R_1$ and $R_2$ is hydrogen; $C_1$-$C_8$alkyl; $C_5$-$C_7$cycloalkyl; phenyl-$C_1$-$C_4$alkyl or phenyl, preferably $C_1$-$C_4$alkyl and, most preferably, methyl or tert-butyl; and the other substituent $R_1$ or $R_2$ is $C_1$-$C_8$alkyl; $C_5$-$C_7$cycloalkyl; phenyl-$C_1$-$C_4$alkyl or phenyl, preferably $C_1$-$C_4$alkyl and, most referably, methyl or tert-butyl;

A is a direct bond or unsubstituted or phenyl-substituted $C_1$-$C_8$alkylene in which, from $C_2$, the alkylene chain may be interrupted by an oxygen or a sulfur atom, and, from $C_3$, the alkylene chain may be straight or branched;

W is a direct bond; —O—CO—; —NH—CO—; —CO—NH—G—; oer —CO—O—G—, wherein G is a direct bond, $C_1$-$C_6$alkylene, $C_5$-$C_8$cycloalkylene, phenylene or the radical —$CH_2$—$C_6H_4$—$CH_2$—, and —CO—NH—G— is able to form a ring with Z;

and

Z is oxygen, sulfur or —N($R_7$)—, wherein $R_7$ is hydrogen, $C_1$-$C_4$alkyl, allyl or benzyl.

b) R is a radical of formula

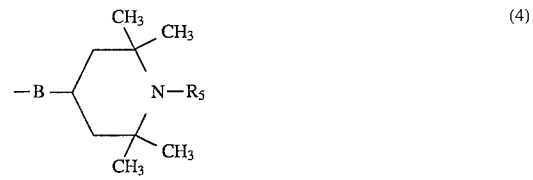

(4)

wherein $R_5$ is hydrogen; oxyl; hydroxy; $C_1$-$C_5$alkyl; $C_2$-$C_5$alkenyl; $C_1$-$C_5$alkoxy; $C_1$-$C_5$alkanoyl; benzoyl or benzyl; and B is oxygen or —N($R_6$)—, wherein $R_6$ is hydrogen or $C_1$-$C_6$alkyl;

c) R is the radical of formula (4) and m=2.

d) A is a direct bond.

e) Z is —N($R_7$)—, wherein $R_7$ is hydrogen, $C_1$-$C_4$alkyl, allyl or benzyl.

f) m=1.

g) $R_3$ is hydrogen.

h) $R_4$ is hydrogen or $C_1$-$C_5$alkyl.

i) $R_5$ is hydrogen or $C_1$-$C_5$alkyl.

Compounds of formula (1) are particularly preferred in which A is a direct bond and Z is —N($R_7$)—, wherein $R_7$ is hydrogen, $C_1$-$C_4$alkyl, allyl or benzyl.

The invention further relates to the process for the preparation of the novel water-soluble antioxidants of formula (1).

The novel water-soluble triazines of formula (1) are conveniently prepared by reacting 1 mol of a 2,4,6-trihalo-s-triazine in succesion with 1 or 2 mol of the compound of formula

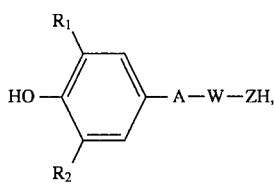

wherein $R_1$, $R_2$, A, W and Z are as defined for formula (1), and with 1 or 2 mol of the compound of formula

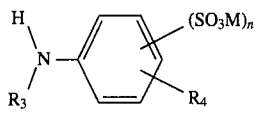

wherein $R_3$, $R_4$, M and n are as defined for formula (1), and, if a compound of each of formula (2a) and (3a) is used, with a compound that introduces the substituent R', and the individual reaction steps may be carried out in any order.

The substituent R' has the meaning assigned to R in formula (1), except the radicals of formulae (2) and (3).

The procedure is normally such that, in the first reaction step, the 2,4,6-trihalo-s-triazine is reacted with the compound having the lesser reactivity.

The reaction temperature is in the range from 0° to 100° C., preferably from 20° to 80° C., and the reaction time is from 1 to 20 hours, preferably from 1 to 4 hours.

The hydrohalic acid generated in the condensation reactions can be neutralised by the final product itself or by addition of a further base, typically aqueous ammonia, an alkali metal hydroxide, an alkali metal carbonate or hydrogen carbonate or an organic base such as triethylamine. The preferred base is an alkali metal carbonate such as sodium carbonate.

The reactions are conveniently carried out in aqueous solution without the addition of organic solvents. The starting 2,4,6-trihalo-s-triazines are known compounds. They are preferably used in the form of aqueous suspensions. A particularly preferred starting compound is cyanuric chloride. The other starting compounds used for the preparation of the compounds of formula (1), typically the compounds that introduce the radicals of formulae (2), (3) or (4), such as metanilic acid, aniline-2,5-disulfonic acid, 2,6-di-tert-butyl-4-aminophenol or 6-(3'-methyl-5'-tert-butyl-4'-hydroxyphenyl)hexanol, are likewise known compounds.

All compounds of formula (1) are preferably prepared as sodium salts, conveniently by dissolving them in the equivalent amount of sodium hydroxide solution and formulating them to solutions, dispersions or emulsions for application.

The novel water-soluble triazines of formula (1) are suitable for enhancing the photochemical and thermal stability of undyed and dyed polyamide fibre materials. The use of the novel compounds for enhancing the photochemical and thermal stability of undyed and dyed polyamide fibre materials accordingly constitutes a further object of the present invention.

The novel compounds of formula (1) can be integrated into standard textile finishing processes for polyamide fibres.

The compounds of formula (1) are applied in the practice of this invention from an aqueous bath which contains the compounds in an amount of 0.005 to 10% by weight, preferably of 0.05 to 2% by weight. The compounds are preferably added to the dyebath. Application can be made before, during or after dyeing by an exhaust or continuous process. Application during dyeing is preferred. The compounds of formula (1) can also be used in conventional print pastes for textile printing.

In the exhaust process, the liquor ratio can vary over a wide range, e.g. from 1:3 to 1:200, preferably from 1:10 to 1:40. The process is conveniently carried out in the temperature range from 20° to 120° C., preferably from 40° to 100° C.

In the continuous process the liquor is conveniently applied to a pick-up of 40–700% by weight, preferably of 40 to 500% by weight. The dyes and antioxidants are then fixed on the fibre material by subjecting the material to a heat treatment. The fixation process can also be carried out by the cold pad-batch method.

The heat treatment of the dyeings obtained in the continuous process and of the prints is preferably carried out by treatment in a steamer with steam or superheated steam in the temperature range from 98° to 105° C. for conveniently 1 to 7, preferably 1 to 5, minutes. The fixation of the dyes by the cold pad-batch method can be effected by storing the impregnated and preferably rolled up goods at room temperature (15° to 30° C.), suitably for 3 to 24 hours, the cold batching time depending naturally on the type of dye to be used.

When the dyeing process and fixation are complete, the dyeings are washed off and dried in conventional manner.

The dyed or undyed polyamide fibre materials obtained by the process of this invention have good photochemical and/or thermal stability.

The dyeings that are photochemically and thermally stabilised in the practice of this invention are those produced with disperse, acid or metal complex dyes, typically azo dyes, 1:2 metal complex dyes such as 1:2 chromium complex, 1:2 cobalt complex or copper complex dyes.

Examples of such dyes are listed in the Colour Index, 3rd Edition 1971, Volume 4.

Polyamide fibre material will be understood as meaning in the context of this invention synthetic polyamide, including polyamide 6, polyamide 66 or polyamide 12, as well as modified, e.g. basic dyeable, polyamide. In addition to pure polyamide fibres, polurethane/polyamide blends, for example tricot material made from polyamide/polyurethane in the ratio 70:30, are also suitable. Basically the pure polyamide material or blends thereof may be in any form of presentation, including fibres, yarn, woven fabrics, knitted fabrics, nonwovens or pile material.

Dyeings obtained on polyamide fibre material by itself or on polyamide/polyurethane or polyamide/polypropylene blends, which material is exposed to heat and/or light and is typically in the form of carpeting, swimwear or car upholstery, is particularly suitable for treatment by the process of this invention.

The process of this invention is most particularly suitable for treating polyamide fibre material that is exposed to the influence of light and heat and is used, for example, as car upholstery or carpeting.

The invention is illustrated by the following Examples in which parts and percentages are by weight.

EXAMPLE 1

A solution of 6.8 g of 3,5-di-tert-butyl-4-hydroxybenzylamine hydrochloride in 75 ml of dioxane/25 ml of water/12.5 ml of 2M aqueous sodium hydroxide is added to a neutral suspension of 15.0 g of a condensate (84.5%) of cyanuric chloride with two equivalents of metanilic acid in 50 ml of water/10 ml of dioxane. With stirring and under nitrogen, the reaction mixture is heated to 60° C. while simultaneously keeping the pH at 8 by the addition of 2M aqueous sodium hydroxide. After 24 hours, the reaction mixture is cooled to room temperature and filtered to remove insoluble matter. The filtrate is acidified with 2M hydrochloric acid to pH 3.5 and 17.5 g of sodium chloride are added at 50° C. The reaction mixture is allowed to cool and the precpitate is isolated by filtration and washed with a mixture of dioxane/10% aqueous solution of sodium chloride for 30 minutes.

The precipitate is vacuum dried at 70° C., affording 7.95 g of a beige powder. This product is further purified by dissolving it hot in 65 ml of a 10% aqueous solution of sodium chloride/15 ml of ethanol/1 g of sodium hydrogen carbonate, acidifying the solution with 2M hydrochloric acid to pH 4 and cooling to room temperature. The precipitate is filtered with suction, washed with a 2% aqueous solution of sodium chloride and vacuum dried at 70° C., affording 3.9 g of a compound of formula

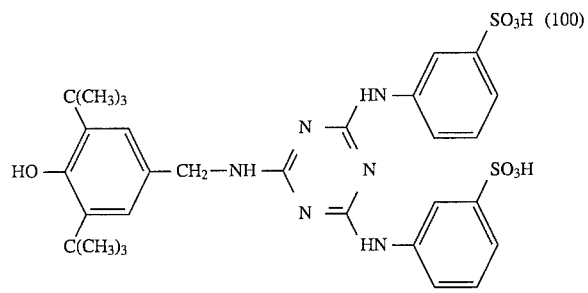

EXAMPLE 2

3.86 g of 2,6-di-tert-butyl-4-aminophenol hydrochloride are added to a neutral suspension of 9.0 g of a condensate (84.5%) of cyanuric chloride with two equivalents of metanilic acid in 100 ml of water/50 ml of dioxane. After blanketing with nitrogen, the pH of the reaction mixture is adjusted to 7.5 by addition of 2M aqueous sodium hydroxide. The reaction mixture is heated to 62°–64° C. and stirred for 18 hours, while keeping the pH at 7.5 by the addition of 2M aqueous sodium hydroxide. The reaction mixture is then cooled to room temperature and extracted with 2×50 ml of ethyl acetate. The aqueous phase is acidified with 2M hydrochloric acid to pH 3 and then a 10% aqueous solution of sodium chloride is added in increments. The precipitate is filtered with suction, washed in succession with 50 ml of a 10% and 25 ml of a 5% aqueous solution of sodium chloride and vacuum dried at 70° C., affording 7.78 g of a compound of formula

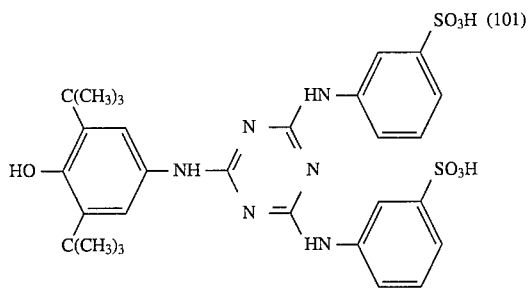

EXAMPLE 3

3.86 g of 2,6-di-tert-butyl-4-aminophenol hyclrochloride and 50 ml of dioxane are added to a solution of 8.67 g of a monocondensate (74%) of cyanuric chloride and aniline-2, 5-disulfonic acid in 100 ml of water. After blanketing with nitrogen, the reaction mixture is made weakly alkaline by the addition of 2M aqueous sodium hydroxide (pH =7.5). The reaction mixture is warmed to 42°–44° C. over 19 hours, while keeping the pH at 7.5 by the continuous addition of 2M aqueous sodium hydroxide. The reaction mixture is thereafter cooled to room temperature and filtered. The filtrate contains the product of formula

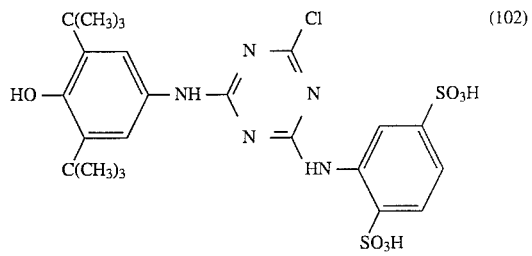

2.34 g of 4-amino-2,2,6,6-tetramethylpiperidine are added at room temperature to the filtrate, and the mixture is heated to 82°–85° C. and kept for 21 hours at this temperature. The reaction solution is concentrated on a rotary evaporator and the residue is dissolved by addition of 4 ml of 2M aqueous sodium hydroxide. To the solution are added 20 g of sodium chloride and 2 ml of ethanol and the batch is then acidified with 2.5 ml of 2M hydrochloric acid. After stirring for 15 hours, the crystalline precipitate is collected by filtration, washed with 10% aqueous sodium chloride solution and vacuum dried at 70° C., affording 8.3 g of a compound of formula

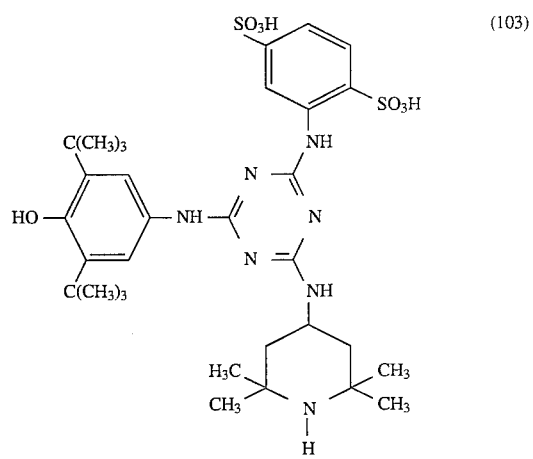

EXAMPLE 4

6.18 g of a condensate of one equivalent of 6-(3'-methyl-5'-tert-butyl-4'-hydroxyphenyl)hexanol and one equivalent of cyanuric chloride are dissolved in 40 ml of acetone and the solution is poured at room temperature into 10 ml of water. The pH is adjusted to 6.5–7 by the dropwise addition of 2M aqueous sodium hydroxide. 2.59 g of metanilic acid, dissolved in 30 ml of 0.5M aqueous sodium hydroxide, are added dropwise to this solution at room temperature and the pH is kept at 7 by the addition of 2M aqueous sodium hydroxide. The reaction mixture is then warmed to 35° C. and kept at this temperature for 3 hours. The product is salted out by the addition of 65 g of conc. aqueous sodium hydroxide for 1 hour. Afterwards the acetone is removed by vacuum distillation. The aqueous dispersion is filtered, and the filter product is washed with 10% aqueous sodium chloride solution and vacuum dried at 40° C., affording a compound of formula

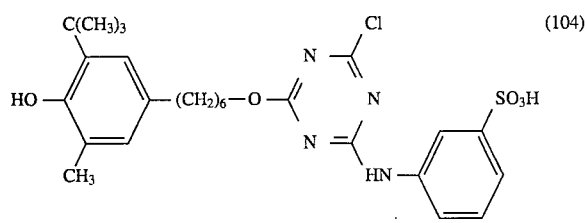

EXAMPLE 5

The procedure of Example 4 is repeated, but using two equivalents instead of one equivalent of metanilic acid and raising the reaction temperature to reflux, to give a compound of formula

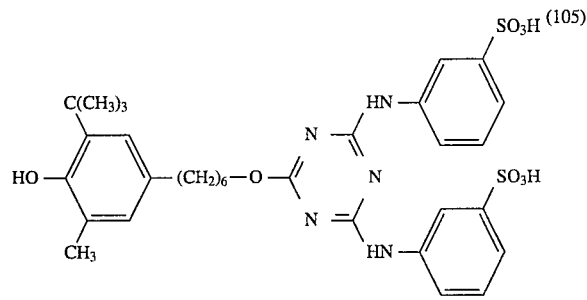

EXAMPLE 6

The procedure of Example 4 is repeated, but replacing the condensate of one equivalent of 6-(3'-methyl-5'-tert-butyl-4'-hydroxyphenyl)hexanol and one equivalent of cyanuric chloride with the equivalent amount of 2,4-dichloro-6-(3',5'-di-tert-butyl-4'-hydroxy)phenoxy-s-triazine to give a compound of formula

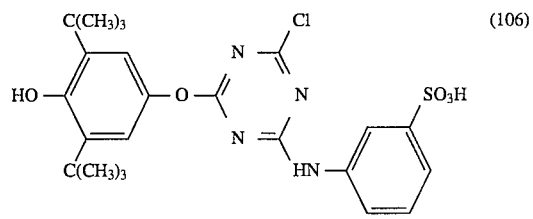

EXAMPLE 7

The procedure of Example 4 is repeated, but replacing the condensate of one equivalent of 6-(3'-methyl-5'-tert-butyl-4'-hydroxyphenyl)hexanol and one equivalent of cyanuric chloride with the equivalent amount of 2,4-dichloro-6-(3', 5'-di-tert-butyl-4'-hydroxy)phenoxy-s-triazine and two equivalents of metanilic acid to give a compound of formula

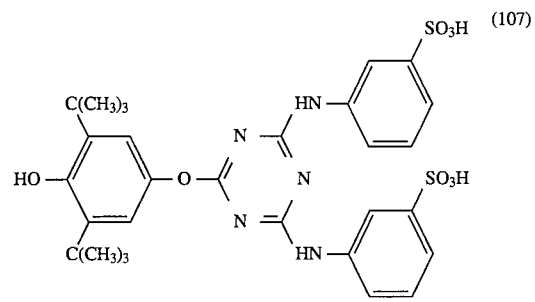

EXAMPLE 8

To a solution of 0.1 mol of cyanuric chloride in 120 ml of acetone are added 3 g of anhydrous sodium sulfate and the mixture is cooled to 0° C. A solution of 0.1 mol of 3,5-di-tert-butyl-4hydroxythiophenol in 25 ml of chlorobenzene is then run in. Afterwards 12.7 g of s-collidine are added dropwise at 5° C. over 20 minutes to the reaction mixture. The reaction is brought to completion by stirring for 30 minutes at 5° C. and for 2 hours at room temperature. The reaction mixture is then filtered and, after washing with 100 ml of acetone, the filtrate is stirred into a mixture of 400 g of ice and 900 ml of water, acidified with dilute hydrochloric acid (weakly acid reaction to litmus paper), and extracted repeatedly with ethyl acetate. Conventional working up and recystallisation from hexane/acetone gives 16.9 g of 2,4-dichloro-6-(3',5'-di-tert-butyl-4'-hydroxyphenylsulfanyl)-s-triazine.

This compound can be reacted in accordance with the procedure described in Example 4 with one equivalent of metanilic acid to give a compound of formula

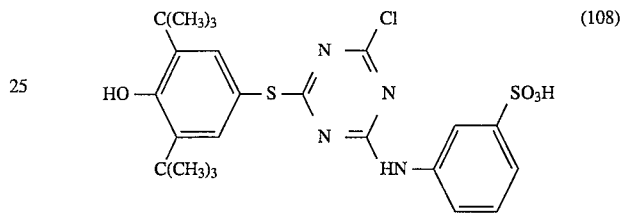

EXAMPLE 9

The procedure described in Example 8 is repeated, but reacting the 2,4-dichloro-6-(3',5'-di-tert-butyl-4'-hydroxyphenylsulfanyl)-s-triazine intermediate in accordance with the procedure described in Example 5 with two equivalents of metanilic acid to give a compound of formula

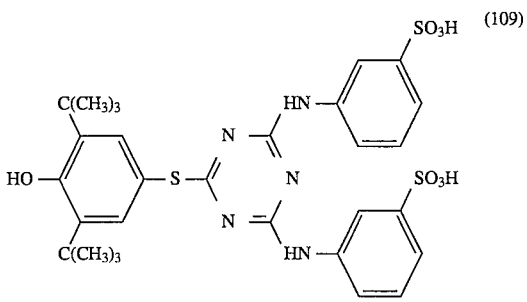

EXAMPLE 10

Three 10 g samples of polyamide 6 knitted fabric are treated in an ®AHIBA dyeing machine at a liquor to goods ratio of 1:30. Liquors 1–3 each contain the following ingredients: 0.5 g/l of monosodium phosphate, 1.5 g/l of disodium phosphate and 1.0% by weight, based on the textile material, of a commercially available levelling agent.

Liquor 2 additionally contains 1.0% by weight, based on the textile material, of the compound of formula (100).

Liquor 3 additionally contains 1.0% by weight, based on the textile material, of the compound of formula (101).

The liquors 1–3 so prepared are warmed to 40° C. After addition of the textile material, treatment is carried out for 10 minutes at this temperature, and the temperature is then raised to 95° C. over 30 minutes. After a treatment time of 10 minutes at 95° C., 2% by weight, based on the textile material, of 80% acetic acid is added to each liquor and treatment is continued for a further 35 minutes. After cooling to 70° C., the samples are rinsed with cold water, centrifuged and dried at 80° C.

Samples 1–3 are then assessed for their photochemical and thermal stability.

a) To test the photochemical stability, pieces measuring 12×8 cm are cut from the treated samples 1 to 3 and exposed for 180 hours in accordance with German standard DIN 75.202 and tested for their tear resistance and elongation in accordance with Swiss standard SN 198.461.

b) To test the thermal stability, the treated samples 1–3 are kept for 96 hours at 150° C. in an oven and then tested for their tear resistance and elongation in accordance with Swiss standard SN 198.461. and for yellowing in accordance with German standard DIN 6167.

Samples 2 and 3 treated with the compounds of formulae (100) and (101) exhibit enhanced tear strength and elongation and lesser yellowing than untreated sample 1.

EXAMPLE 11

Three 10 g samples of polyamide 6 knitted fabric are treated in an ®AHIBA dyeing machine at a liquor to goods ratio of 1:30. Liquors 1a–3a each contain the following ingredients: 0.5 g/l of monosodium phosphate, 1.5 g/l of disodium phosphate and 1.0% by weight, based on the textile material, of a commercially available levelling agent, 0.032% by weight of the dye of formula (I), 0.005% by weight of the dye of formula (II) and 0.002% by weight of the dye of formula (III) (the percentages are in each case based on the weight of the material to be dyed) in dissolved form:

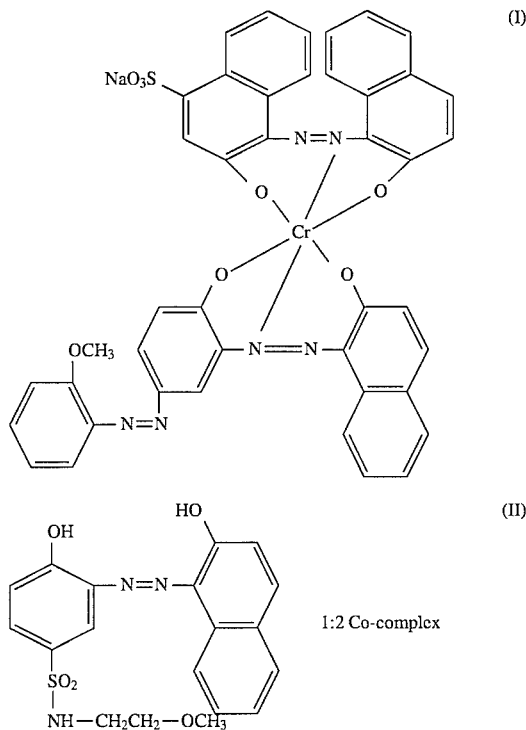

and

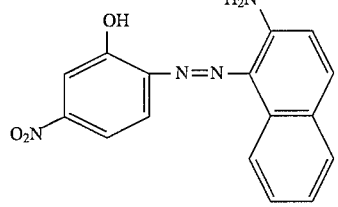

and 0.003%, based on the the material to be dyed, of a commercial surfactant.

Liquor 2a additionally contains 1.0% by weight, based on the textile material, of the compound of formula (100).

Liquor 3a additionally contains 1.0% by weight, based on the textile material, of the compound of formula (101).

The dye liquors are warmed to 45° C. After addition of the textile material, treatment is carried out for 10 minutes at this temperature, and the temperature is then raised to 95° C. over 30 minutes. After a dyeing time of 10 minutes at 95° C., 2% by weight, based on the textile material, of 80% acetic acid is added and dyeing is continued for a further 35 minutes. After cooling to 70° C., the dyed material is rinsed with cold water and dried at 80° C.

The lightfastness of the samples 1a–3a is then tested in accordance with two different standards
a) German standard DIN 75.202 (FAKRA) and b) US standard SAEJ 1885.

Samples 2a and 3a treated with the compounds of formulae (100) and (101) exhibit better lightfastness than untreated sample 1a.

EXAMPLE 12

Three 10 g samples of polyamide 6 knitted fabric are treated in an ®AHIBA dyeing machine at a liquor to goods ratio of 1:30. Liquors 1b–3b each contain the following ingredients: 0.5 g/l of monosodium phosphate, 1.5 g/l of disodium phosphate and 1.0% by weight, based on the textile material, of a commercially available levelling agent.

Liquor 2b additionally contains 0.5% by weight, based on the textile material, of the compound of formula (103).

Liquor 3b additionally contains 1.0% by weight, based on the textile material, of the compound of formula (103).

The liquors 1b–3b so prepared are warmed to 40° C., the fibre material is added and treated as described in Example 10.

Samples 1b–3b are then tested for their photochemical and thermal stability.

a) To test the photochemical stability, pieces measuring 12×8 cm are cut from treated samples 1b–3b and exposed for 180 hours in accordance with German standard DIN 75.202 and tested for their tear resistance and elongation in accordance with Swiss standard SN 198.461.

b) To test the thermal stability, the treated samples 1b–3b are kept for 96 hours at 150° C. in an oven and then tested for their tear resistance and elongation in accordance with Swiss standard SN 198.461. and for yellowing in accordance with German standard DIN 6167.

Samples 2b and 3b treated with the compound of formula (103) exhibit better photochemical and thermal stability than untreated sample 1b.

EXAMPLE 13

Three 10 g samples of polyamide 6 knitted fabric are treated in an ®AHIBA dyeing machine at a liquor to goods ratio of 1:30. Liquors 1c–3c each contain the following ingredients: 0.5 g/l of monosodium phosphate, 1.5 g/l of disodium phosphate and 1.0% by weight, based on the textile material, of a commercially available levelling agent, 0.032% by weight of the dye of formula (I) and 0.005% by weight of the dye of formula (III) (the percentages are in each case based on the weight of the material to be dyed) in dissolved form.

Liquor 2c additionally contains 0.5% by weight, based on the textile material, of the compound of formula (103).

Liquor 3c additionally contains 1.0% by weight, based on the textile material, of the compound of formula (103).

The dye liquors are warmed to 45° C., the fibre material is added and dyed as described in Example 11.

The lightfastness of the samples 1c–3c is then tested in accordance with two different standards a) German standard DIN 75.202 (FAKRA) and b) US standard SAEJ 1885.

Samples 2c and 3c treated with the compound of formula (103) exhibit better lightfastness than untreated sample 1c.

EXAMPLE 14

Seven 10 g samples of polyamide 6 knitted fabric are treated in an ®AHIBA dyeing machine at a liquor to goods ratio of 1:30. Liquors 1d–7d each contain the following ingredients: 0.5 g/l of monosodium phosphate, 1.5 g/l of disodium phosphate and 1.0% by weight, based on the textile material, of a commercially available levelling agent.

Liquor 2d additionally contains 0.5% by weight, based on the textile material, of the compound of formula (104).

Liquor 3d additionally contains 0.5% by weight, based on the textile material, of the compound of formula (105).

Liquor 4d additionally contains 0.5% by weight, based on the textile material, of the compound of formula (106).

Liquor 5d additionally contains 0.5% by weight, based on the textile material, of the compound of formula (107).

Liquor 6d additionally contains 0.5% by weight, based on the textile material, of the compound of formula (108).

Liquor 7d additionally contains 0.5% by weight, based on the textile material, of the compound of formula (109).

The liquors 1b–3b so prepared are warmed to 40° C., the fibre material is added and treated as described in Example 10.

Samples 1d–7d are then tested for their photochemical and thermal stability.

a) To test the photochemical stability, pieces measuring 12×8 cm are cut from treated samples 1d–7d and exposed for 180 hours in accordance with German standard DIN 75.202 and tested for their tear resistance and elongation in accordance with Swiss standard SN 198.461.

b) To test the thermal stability, the treated samples 1d–7d are kept for 96 hours at 150° C. in an oven and then tested for their tear resistance and elongation in accordance with Swiss standard SN 198.461. and for yellowing in accordance with German standard DIN 6167.

Samples 2d to 7d treated with the compounds of formulae (104) to (109) exhibit better photochemical and thermal stability than untreated sample 1d.

What is claimed is:

1. A water-soluble antioxidant of formula

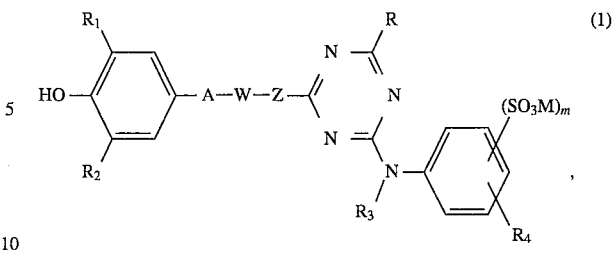

wherein

R is halogen; $C_1$–$C_5$alkyl; phenyl-$C_1$–$C_5$alkyl; $C_1$–$C_5$alkoxy in which, from $C_2$, the alkyl chain may be interrupted by an oxygen or a sulfur atom; $C_3$–$C_5$alkenyloxy; $C_4$–$C_8$cycloalkoxy; amino; mono- or di(phenyl-$C_1$–$C_5$alkyl)amino; unsubstituted or hydroxy- or carboxy-substituted mono- or di-$C_1$–$C_5$alkylamino, in which the alkyl chain may be interrupted by an oxygen or a sulfur atom or by $SO_2$; mono- or di-$C_3$–$C_5$alkenyl-amino; unsubstituted or $C_1$–$C_5$alkyl-substituted mono- or di-$C_4$–$C_8$cycloalkylamino; unsubstituted phenoxy or phenoxy which is substituted by halogen, $C_1$–$C_5$alkyl, $C_1$–$C_5$alkoxycarbonyl, $C_1$–$C_5$alkoxy, carboxy, carbamoyl, mono- or di-$C_1$–$C_5$alkanoyl-amino or $C_1$–$C_5$alkanoyl; phenyl; phenylthio; phenyl-$C_1$–$C_5$alkylthio; $C_1$–$C_5$alkylthio; $C_4$–$C_8$cycloalkylthio; unsubstituted or $C_1$–$C_5$alkyl-, hydroxy- or carboxy-substituted 1-azacycloalkyl; unsubstituted or $C_1$–$C_5$alkyl-substituted morpholino; a radical of formula

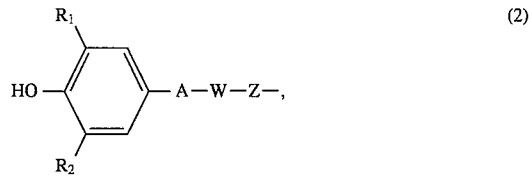

a radical of formula

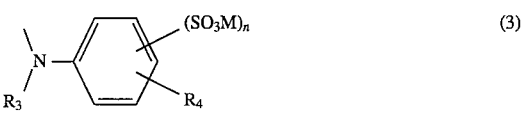

or a radical of formula

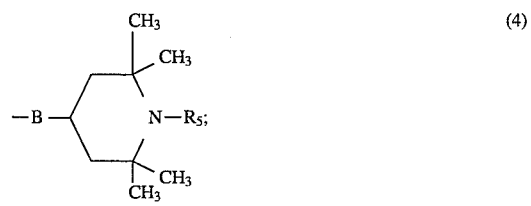

wherein one of the two substituents $R_1$ and $R_2$ is hydrogen; $C_1$–$C_8$alkyl; $C_5$–$C_7$cycloalkyl; phenyl-$C_1$–$C_4$alkyl or phenyl; and the other substituent $R_1$ or $R_2$ is $C_1$–$C_8$alkyl; $C_5$–$C_7$cycloalkyl; phenyl-$C_1$–$C_4$alkyl or phenyl;

$R_3$ is hydrogen or $C_1$–$C_4$alkyl;

$R_4$ is hydrogen; halogen; hydroxy; $C_1$–$C_5$alkyl; $C_1$–$C_5$alkoxycarbonyl; $C_1$–$C_5$alkoxy; $C_1$–$C_5$alkanoyl; carboxy; amino; mono- or di-$C_1$–$C_5$alkylamino; or mono- or di-$C_1$–$C_5$-alkanoylamino;

$R_5$ is hydrogen; oxyl; hydroxy; $C_1$–$C_5$alkyl; $C_2$–$C_5$alkenyl; $C_1$–$C_5$alkoxy; $C_1$–$C_5$alkanoyl; benzoyl or benzyl;

m is 0, 1 or 2;

n is 0, 1 or 2;

and the sum m+n is 1, 2, 3 or 4;

M may be the same or different and is hydrogen; an alkali metal, alkaline earth metal or ammonium cation or an organic ammonium cation of formula $(C_1$–$C_4 alkyl)_a(H)_b N^+$, wherein a is an integer from 0 to 3;

b is an integer from 1 to 4; and the sum of a+b=4;

A is a direct bond or unsubstituted or phenyl-substituted $C_1$–$C_8$alkylene in which, from $C_2$, the alkylene chain may be interrupted by an oxygen or a sulfur atom, and, from $C_3$, the alkylene chain may be straight or branched;

B is oxygen or —N($R_6$)—, wherein $R_6$ is hydrogen or $C_1$–$C_6$alkyl;

W is a direct bond; —O—CO—; —NH—CO—; —CO—NH—G—; or —CO—O—G—, wherein G is a direct bond, $C_1$–$C_6$alkylene, $C_5$–$C_8$cycloalkylene, phenylene or the radical —CH$_2$—C$_6$H$_4$—CH$_2$—, and —CO—NH—G— is able to form a ring with Z;

and

Z is oxygen, sulfur or —N($R_7$)—, wherein $R_7$ is hydrogen, $C_1$–$C_4$alkyl, allyl or benzyl.

2. A water-soluble antioxidant according to claim 1, wherein R is a radical of formula $$\text{HO} - \underset{R_2}{\overset{R_1}{\bigcirc}} - A-W-Z-, \quad (2)$$

wherein one of the two substituents $R_1$ and $R_2$ is hydrogen; $C_1$–$C_8$alkyl; $C_5$–$C_7$cycloalkyl; phenyl-$C_1$–$C_4$alkyl or phenyl; and the other substituent $R_1$ or $R_2$ is $C_1$–$C_8$alkyl; $C_5$–$C_7$cycloalkyl; phenyl-$C_1$–$C_4$alkyl or phenyl;

A is a direct bond or unsubstituted or phenyl-substituted $C_1$–$C_8$alkylene in which, from $C_2$, the alkylene chain may be interrupted by an oxygen or a sulfur atom, and, from $C_3$, the alkylene chain may be straight or branched;

W is a direct bond; —O—CO—; —NH—CO—; —CO—NH—G—; or —CO—O—G—, wherein G is a direct bond, $C_1$–$C_6$alkylene, $C_5$–$C_8$cycloalkylene, phenylene or the radical —CH$_2$—C$_6$H$_4$—CH$_2$—, and —CO—NH—G— may form a ring with Z;

and

Z is oxygen, sulfur or —N($R_7$)—, wherein $R_7$ is hydrogen, $C_1$–$C_4$alkyl, allyl or benzyl.

3. A water-soluble antioxidant according to claim 2, wherein $R_1$ and $R_2$ are each independently of the other $C_1$–$C_4$alkyl.

4. A water-soluble antioxidant according to claim 3, wherein $R_1$ and $R_2$ are each independently of the other methyl or tert-butyl.

5. A water-soluble antioxidant according to claim 1, wherein m is 1.

6. A water-soluble antioxidant according to claim 1, wherein R is a radical of formula $$-B-\underset{CH_3 \quad CH_3}{\overset{CH_3 \quad CH_3}{\bigcirc}}N-R_5 \quad (4)$$

$R_5$ is hydrogen; oxyl; hydroxy; $C_1$–$C_5$alkyl; $C_2$–$C_5$alkenyl; $C_1$–$C_5$alkoxy; $C_1$–$C_5$alkanoyl; benzoyl or benzyl;

B is oxygen or —N($R_6$)—, wherein $R_6$ is hydrogen or $C_1$–$C_6$alkyl.

7. A water-soluble antioxidant according to claim 6, wherein m is 2.

8. A water-soluble antioxidant according to claim 1, wherein A is a direct bond.

9. A water-soluble antioxidant according to claim 1, wherein Z is —N($R_7$)—, wherein $R_7$ is hydrogen, $C_1$–$C_4$alkyl, allyl or benzyl.

10. A water-soluble antioxidant according to claim 1, wherein A is a direct bond and Z is —N($R_7$)—, wherein $R_7$ is hydrogen, $C_1$–$C_4$alkyl, allyl or benzyl.

11. A water-soluble antioxidant according to claim 1, wherein $R_3$ is hydrogen.

12. A water-soluble antioxidant according to claim 1, wherein $R_4$ is hydrogen or $C_1$–$C_5$alkyl.

13. A water-soluble antioxidant according to claim 1, wherein $R_5$ is hydrogen or $C_1$–$C_5$alkyl.

14. A water-soluble antioxidant according to claim 1, wherein R is chloro; a radical of formula (3), wherein $R_3$ and $R_4$ are hydrogen and n=1; or a radical of formula (4), wherein $R_5$ is hydrogen and B is —NH—;

$R_1$ is —C(CH$_3$)$_3$;

$R_2$ is —CH$_3$; or —C(CH$_3$)$_3$;

m is 1 or 2;

M is a sodium cation;

A is a direct bond; —CH$_2$—; or —(CH$_2$)$_6$—;

W is a direct bond; —O—CO—; —NH—CO—; —CO—NH—G—; or —CO—O—G—, wherein G is a direct bond, $C_1$–$C_6$alkylene, $C_5$–$C_8$cycloalkylene, phenylene or the radical —CH$_2$—C$_6$H$_4$—CH$_2$—, and —CO—NH—G—is able to form a ring with Z;

and

Z is oxygen, sulfur or —NH—.

15. A process for the preparation of a water-soluble antioxidant of formula $$\text{HO} - \underset{R_2}{\overset{R_1}{\bigcirc}} - A-W-Z-\underset{N}{\overset{N}{\underset{\underset{R_3}{|}}{=}}}\underset{R_4}{\overset{R}{\bigcirc}}(SO_3M)_m, \quad (1)$$

wherein

R is halogen; $C_1$–$C_5$alkyl; phenyl-$C_1$–$C_5$alkyl; $C_1$–$C_5$alkoxy in which, from $C_2$, the alkyl chain may be interrupted by an oxygen or a sulfur atom;

$C_3$–$C_5$alkenyloxy; $C_4$–$C_8$cycloalkoxy; amino; mono- or di(phenyl-$C_1$–$C_5$alkyl)amino; unsubstituted or hydroxy- or carboxy-substituted mono- or di-$C_1$–$C_5$alkylamino, in which the alkyl chain may be interrupted by an oxygen or a sulfur atom or by $SO_2$; mono- or di-$C_3$–$C_5$alkenyl-amino; unsubstituted or $C_1$–$C_5$alkyl-substituted mono- or di-$C_4$–$C_8$cycloalkylamino; unsubstituted phenoxy or phenoxy which is substituted by halogen, $C_1$–$C_5$alkyl, $C_1$–$C_5$alkoxycarbonyl, $C_1$–$C_5$alkoxy, carboxy, carbamoyl, mono- or di-$C_1$–$C_5$alkanoyl-amino or $C_1$–$C_5$alkanoyl; phenyl; phenylthio; phenyl-$C_1$–$C_5$alkylthio; $C_1$–$C_5$alkylthio; $C_4$–$C_8$cycloalkylthio; unsubstituted or $C_1$–$C_5$alkyl-, hydroxy- or carboxy-substituted 1-azacycloalkyl; unsubstituted or $C_1$–$C_5$alkyl-substituted morpholino; a radical of formula

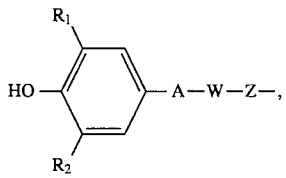
(2)

a radical of formula

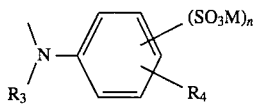
(3)

or a radical of formula

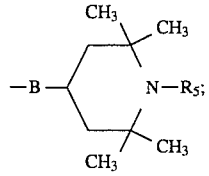
(4)

wherein one of the two substituents $R_1$ and $R_2$ is hydrogen; $C_1$–$C_8$alkyl; $C_5$–$C_7$cycloalkyl; phenyl-$C_1$–$C_4$alkyl or phenyl; and the other substituent $R_1$ or $R_2$ is $C_1$–$C_8$alkyl; $C_5$–$C_7$cycloalkyl; phenyl-$C_1$–$C_4$alkyl or phenyl;

$R_3$ is hydrogen or $C_1$–$C_4$alkyl;

$R_4$ is hydrogen; halogen; hydroxy; $C_1$–$C_5$alkyl; $C_1$–$C_5$alkoxycarbonyl; $C_1$–$C_5$alkoxy; $C_1$–$C_5$alkanoyl; carboxy; amino; mono- or di-$C_1$–$C_5$alkylamino; or mono- or di-$C_1$–$C_5$-alkanoylamino;

$R_5$ is hydrogen; oxyl; hydroxy; $C_1$–$C_5$alkyl; $C_2$–$C_5$alkenyl; $C_1$–$C_5$alkoxy; $C_1$–$C_5$alkanoyl; benzoyl or benzyl;

m is 0, 1 or 2;

n is 0, 1 or 2;

and the sum m+n is 1, 2, 3 or 4;

M may be the same or different and is hydrogen; an alkali metal, alkaline earth metal or ammonium cation or an organic ammonium cation of formula

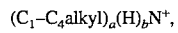

wherein a is an integer from 0 to 3;

b is an integer from 1 to 4; and the sum of a+b=4;

A is a direct bond or unsubstituted or phenyl-substituted $C_1$–$C_8$alkylene in which, from $C_2$, the alkylene chain may be interrupted by an oxygen or a sulfur atom, and, from $C_3$, the alkylene chain may be straight or branched;

B is oxygen or —N($R_6$)—, wherein $R_6$ is hydrogen or $C_1$–$C_6$alkyl;

W is a direct bond; —O—CO—; —NH—CO—; —CO—NH—G—; or —CO—O—G—, wherein G is a direct bond, $C_1$–$C_6$alkylene, $C_5$–$C_8$cycloalkylene, phenylene or the radical —$CH_2$—$C_6H_4$—$CH_2$—, and —CO—NH—G— is able to form a ring with Z;

and

Z is oxygen, sulfur or —N($R_7$)—, wherein $R_7$ is hydrogen, $C_1$–$C_4$alkyl, allyl or benzyl, which process comprises reacting 1 mol of a 2,4,6-trihalo-s-triazine in succession with 1 or 2 mol of the compound of formula

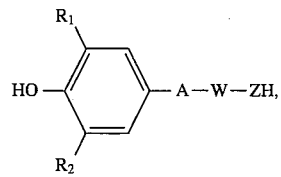
(2a)

wherein $R_1$, $R_2$, A, W and Z are as defined for formula (1), and with 1 or 2 mol of the compound of formula

(3a)

wherein $R_3$, $R_4$, M and n are as defined for formula (1), and, if a compound of each of formula (2a) and (3a) is used, with a compound that introduces the substituent R', wherein R' has the meaning of R in formula (1), except for the radicals of formulae (2) and (3).

16. A process for the photochemical and thermal stabilisation of polyamide fibre materials, which comprises treating dyed or undyed polyamide fibre materials with a water-soluble antioxidant of formula (1) as claimed in claim 1.

17. A process as claimed in claim 16 for the photochemical and thermal stabilization of polyamide fibre materials wherein the polyamide fibre materials are selected from the group consisting of polyamides, a blend of polyamide and polyurethane and a blend of polyamide and polypropylene.

18. Fibre material treated with a water-soluble antioxidant of formula (1) which is prepared by the method as claimed in claim 16.

\* \* \* \* \*